(12) United States Patent
Marik et al.

(10) Patent No.: US 8,206,419 B2
(45) Date of Patent: *Jun. 26, 2012

(54) SYSTEMS AND DEVICES FOR DYNAMIC STABILIZATION OF THE SPINE

(75) Inventors: Greg C. Marik, Collierville, TN (US); Julien J. Prevost, Memphis, TN (US); Jayant Jangra, Memphi, TN (US); Henry K. Bonin, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 255 days.

This patent is subject to a terminal disclaimer.

(21) Appl. No.: 12/422,606

(22) Filed: Apr. 13, 2009

(65) Prior Publication Data

US 2010/0262187 A1 Oct. 14, 2010

(51) Int. Cl.
*A61B 17/70* (2006.01)
(52) U.S. Cl. ........................................ 606/247
(58) Field of Classification Search ........... 606/246–279
See application file for complete search history.

(56) References Cited

U.S. PATENT DOCUMENTS

| | | | |
|---|---|---|---|
| 5,480,401 A | 1/1996 | Navas | |
| 7,175,622 B2 | 2/2007 | Farris | |
| 7,291,150 B2 | 11/2007 | Graf | |
| 2004/0049190 A1 | 3/2004 | Biedermann et al. | |
| 2004/0143264 A1 | 7/2004 | McAfee | |
| 2004/0225289 A1 | 11/2004 | Biedermann et al. | |
| 2005/0113927 A1 | 5/2005 | Malek | |
| 2006/0082987 A1 | 4/2006 | Dorsey et al. | |
| 2006/0113927 A1 | 6/2006 | Bondy et al. | |
| 2006/0264940 A1 | 11/2006 | Hartmann | |
| 2006/0293657 A1 | 12/2006 | Hartmann | |
| 2006/0293663 A1 | 12/2006 | Walkenhorst et al. | |
| 2007/0029362 A1 | 2/2007 | Caillaud et al. | |
| 2007/0049936 A1 | 3/2007 | Colleran et al. | |
| 2007/0078461 A1 | 4/2007 | Shluzas | |
| 2007/0100341 A1 | 5/2007 | Reglos et al. | |
| 2007/0161997 A1 | 7/2007 | Thramann et al. | |
| 2007/0233085 A1 | 10/2007 | Biedermann et al. | |
| 2007/0233091 A1 | 10/2007 | Naifeh et al. | |
| 2007/0270810 A1 | 11/2007 | Sanders | |
| 2007/0270814 A1 | 11/2007 | Lim et al. | |
| 2007/0270837 A1 | 11/2007 | Eckhardt et al. | |
| 2007/0270838 A1 | 11/2007 | Bruneau et al. | |
| 2007/0288009 A1 | 12/2007 | Brown et al. | |

(Continued)

OTHER PUBLICATIONS

Response to Office Action for U.S. Appl. No. 12/422,387, filed Jun. 22, 2011.

(Continued)

*Primary Examiner* — Eduardo C Robert
*Assistant Examiner* — Stuart S Bray

(57) ABSTRACT

A dynamic stabilization device, system, and method for use with a spinal motion segment includes a first bone anchor assembly, a second bone anchor assembly, a first articulation element and a second articulation element. The first articulation element includes an end portion engageable with the first bone anchor assembly, a first articulation surface, and a resilient element therebetween. The first articulation surface is separably engageable with a second articulation surface associated with the second articulation element. The resilient element provides resilient resistance when the first and second bone anchor assemblies are moved toward one another and provides no resistance and is separable from the second bone anchor assembly when the first and second bone anchor assemblies are moved away from one another.

20 Claims, 4 Drawing Sheets

U.S. PATENT DOCUMENTS

| | | |
|---|---|---|
| 2008/0021459 A1 | 1/2008 | Lim |
| 2008/0039847 A1 | 2/2008 | Piper et al. |
| 2008/0065073 A1 | 3/2008 | Perriello et al. |
| 2008/0183213 A1 | 7/2008 | Veldman et al. |
| 2008/0234739 A1* | 9/2008 | Hudgins et al. ............... 606/255 |
| 2008/0275504 A1* | 11/2008 | Bonin et al. .................. 606/246 |
| 2009/0018585 A1* | 1/2009 | Reiley ........................... 606/248 |
| 2009/0088799 A1* | 4/2009 | Yeh ............................... 606/246 |
| 2010/0094344 A1* | 4/2010 | Trieu ............................. 606/246 |
| 2010/0262191 A1* | 10/2010 | Marik et al. ................... 606/264 |
| 2010/0262192 A1* | 10/2010 | Foley ............................ 606/264 |

OTHER PUBLICATIONS

Response to Office Action for U.S. Appl. No. 12/422,367, filed Jun. 23, 2011.

* cited by examiner

SYSTEMS AND DEVICES FOR DYNAMIC STABILIZATION OF THE SPINE

BACKGROUND

Elongated connecting elements, such as rods, plates, tethers, wires, cables, and other devices have been implanted along the spinal column and connected between two or more anchors engaged between one or more spinal motion segments. Some connecting elements provide a rigid construct that resists movement of the spinal motion segment in response to spinal loading or movement of the spinal motion segment by the patient. Still other connecting elements are flexible to permit at least limited spinal motion while providing resistance to loading and motion of the spinal motion segment. Such flexible connecting elements can be considered to provide dynamic spinal stabilization since at least limited movement of the spinal motion segment is preserved after implantation of the connecting element.

SUMMARY

The present invention generally relates to systems, devices, and methods for dynamically stabilizing a spinal column motion segment including at least two vertebrae by engaging a resilient element between the two vertebrae. An exemplary device includes two separably engageable articulation surfaces positioned between the two vertebrae with a resilient element associated with at least one of the articulation surfaces.

In one aspect, a spinal stabilization system for dynamically stabilizing a first vertebral body with respect to a second vertebral body includes first and second bone anchor assemblies engageable with respective ones of first and second substrates, such as vertebral bodies, and first and second articulation elements attachable to the first and second bone anchor assemblies, respectively. The first articulation element includes an end portion, a first articulation surface, and a resilient element disposed between the end portion and the first articulation surface. The second articulation element includes a second articulation surface configured to engage the first articulation surface. In this aspect, the first articulation surface is configured to be separably engageable with the second articulation surface and is positioned between the end portion of the first articulation element and the second articulation surface. The resilient element is configured to resiliently resist movement of the first bone anchor assembly and the second bone anchor assembly towards each other when the first articulation surface and the second articulation surface are engaged with each other and the first articulation element and the second articulation element are attached to the first bone anchor assembly and the second bone anchor assembly, respectively. Stated alternatively, the resilient element is configured to resiliently compress when the first articulation element and the second articulation element are engaged and force is provided to press the first articulation element and the second articulation element together. The first articulation element and the second articulation element are configured to provide no resistance to the movement of the first bone anchor assembly and the second bone anchor assembly away from each other or to movement of the first articulation surface and the second articulation surface away from one another.

In another aspect, a device for use in a dynamic spinal stabilization system includes a first articulation element and a second articulation element. The first articulation element includes an end portion, a first articulation surface, and a resilient element disposed between the end portion and the first articulation surface. The second articulation element includes a second articulation surface configured to engage the first articulation surface. In this aspect, the first articulation surface is configured to be separably engageable with the second articulation surface and is positioned between the end portion of the first articulation element and the second articulation surface. The resilient element is configured to resiliently resist compression of the first articulation surface against the second articulation surface when they are engaged with each other.

In yet another aspect, a method for installing a dynamic stabilization system includes installing a first anchor assembly into a first substrate and a second anchor assembly into a second substrate. A first articulation element having an end portion and a resilient element is positioned such that the end portion is connectable to the first bone anchor assembly and such that the first articulation element is separably engageable with a second articulation element attached to the second bone anchor assembly. The method further includes connecting the end portion to the first bone anchor assembly. The resilient element is configured to resiliently resist movement of the first bone anchor assembly and the second bone anchor assembly toward each other when the first articulation element and the second articulation element are engaged while providing no resistance to the movement of the first bone anchor assembly and the second bone anchor assembly away from each other.

These and other aspects are described below.

DESCRIPTION OF THE ILLUSTRATED EMBODIMENTS

Figure 1:
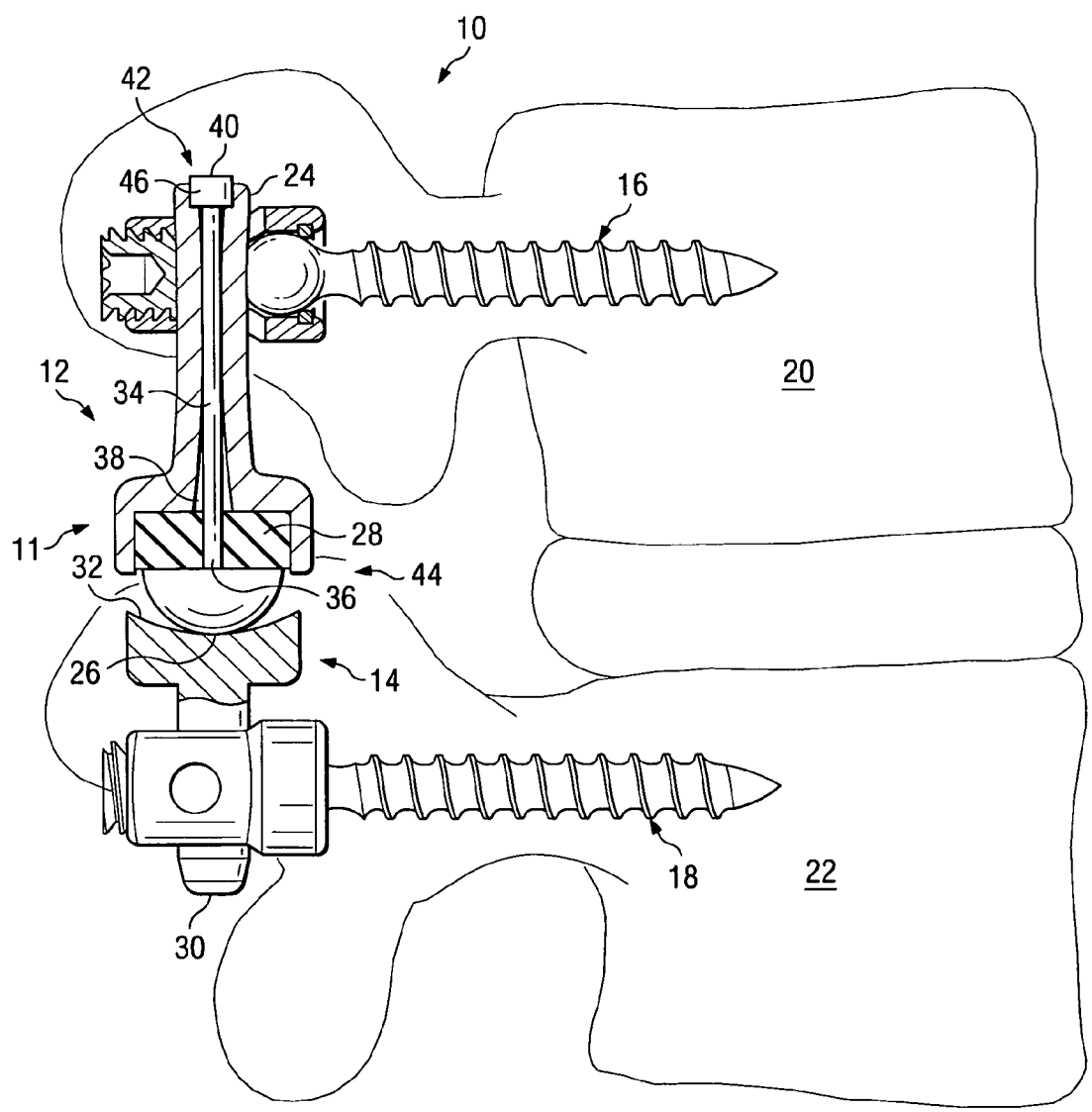
FIG. 1 is an elevational view in partial cross-section of a dynamic stabilization system and device according to one embodiment of the present invention in a neutral position.

The present disclosure relates generally to the field of orthopedic surgery, and more particularly to systems and methods for stabilizing a spinal joint or spinal motion segment. For the purposes of promoting an understanding of the principles of the invention, reference will now be made to the embodiments illustrated in the drawings and specific language will be used to describe the same. It will nevertheless be understood that no limitation of the scope of the invention is thereby intended. Alterations and further modifications in the illustrated devices, as well as further applications of the principles of the invention as illustrated herein, are contemplated as would normally occur to one skilled in the art to which the invention relates.

Systems, devices, and methods for providing dynamic stabilization of one or more spinal motion segments are provided. The systems and devices include a device with a first articulation element and a second articulation element that is configured to be disposed between at least two bone anchor assemblies that can be attached to at least two or more vertebral bodies of a spinal motion segment. The device extends along a longitudinal axis and the first articulation element includes an end portion engageable to one of the anchor assemblies, a first articulation surface, and a resilient element therebetween that is attached to the end portion. The first articulation surface communicates, such as through abutment, with a second articulation surface on the second articulation element to provide a stabilization construct that is movable in response to at least spinal extension, spinal flexion, and lateral bending of the spinal column. The resilient element, or bumper assembly, between the first articulation surface and the end portion defines multiple planes and locations of motion relative to the longitudinal axis of the device while providing appropriate stiffness and resistance for spinal stabilization as the spinal motion segment deviates from the neutral position and the bone anchor assemblies move closer together.

The anchor assemblies discussed herein can be multi-axial or uni-axial in form, and can include an anchor member engageable to a vertebral body and a receiver, post or other device for receiving, connecting, or engaging the first articulation element or the second articulation element. The multi-axial anchor assemblies allow the anchor member to be positioned at various angles relative to the articulation element. The uni-axial anchor assemblies can provide a fixed positioning of the articulation element to the anchor member. The anchor member of the anchor assemblies can form a distal lower portion that is engageable to a substrate, such as a vertebral body, with the proximal connecting portion positioned adjacent the vertebral body.

The first and the second anchor assemblies can be the same or different. The first anchor assembly is configured to attach or connect to the end portion. In some embodiments, the second anchor assembly is configured to attach to the second articulation element. In some embodiments the second anchor assembly includes a second articulation surface to cooperate with the first articulation surface. In some embodiments the second anchor assembly includes a head, post, cup, or other structure to provide the second articulation surface for engagement with the first articulation surface.

In one embodiment, the first and/or second anchor assembly is in the form of a bone screw with a threaded shaft and a proximal head that is pivotally attached thereto, such as a pedicle screw. In other embodiments, the anchor member can be in the form of a hook, staple, cable, tether, suture anchor, interbody fusion implant, artificial disc implant, bolt, or other structure engageable to bony tissue. The connecting portion can include a receiver with a U-shape, O-shape, or other shape that defines a passage that receives the respective end member of the connecting element therein, thereon, therethrough, or thereover, for example.

FIG. 1 illustrates one embodiment of a bone anchor-based dynamic stabilization system 10 in accordance with the present invention. A first articulation element 12 and a second articulation element 14 are attached to a first bone anchor assembly 16 and a second bone anchor assembly 18, respectively. The first bone anchor assembly 16 is engageable to a first vertebra 20 and the second bone anchor assembly 18 is engageable to a second vertebra 22. The first articulation element 12 includes an end portion 24, a first articulation surface 26, and a resilient element 28 disposed therebetween. The second articulation element 14 includes a post 30 and a second articulation surface 32. The end portion 24 is attached to the first bone anchor assembly 16 and the post 30 is attached to the second bone anchor assembly 18.

In one embodiment, the first articulation surface 26 is secured to the end portion 24, such as via a connector 34. The connector 34 engages the first articulation surface and is disposed through a first passage 36 through the resilient element 28 and into a second passage 38 in the end portion 24. The connector 34 is secured in the end portion 24, such as by crimping within the second passage 38 or by a head, ferrule, or stop member 40 disposed at a proximal end 42 of the end portion that retains the first articulation surface 26 and the end portion 24 together.

In some embodiments, the connector 34 is integral with the first articulation surface 26, and in some embodiments, the connector 34 is separate from but attached, secured, or otherwise engaged to the first articulation surface 26. The first passage 36 and the second passage 38 may extend completely through the resilient element 28 and end portion 24, respectively, or may extend only partially therethrough. For example, if the connector 34 is crimped in the end portion 24, then the first passage 36 will extend completely through the resilient element 28 and the second passage 38 need only extend partially through the end portion 24. If the connector is crimped in the resilient element 28, then the first passage 36 extends only partially through the resilient element 28 and the second passage 38 does not need to be present in the end portion 24. If the connector 34 is provided with a head 40 to secure the first articulation surface 26 to the end portion 24, then the first passage extends through the resilient element 28 and the second passage 38 extends through the end portion 24. These and other configurations are within the spirit and scope of the invention and can be selected by one of ordinary skill in the art to accommodate the particular circumstances in which the present invention will be utilized.

Various embodiments of crimping and disposition of the connector 34 within the passages 36, 38 are described in U.S. Ser. No. 11/028,999, filed Jan. 4, 2005, which is incorporated herein by reference in its entirety.

In embodiments having a head 40, the connector 34 extends from the first articulation surface 26, through the first passage 36 in the resilient element 28, through the second passage 38 in the end portion 24, to terminate in the head 40. The head 40 is disposed at the proximal end 42 of the end portion 24 and is prevented from moving toward the distal end 44 of the end portion 24 by a shoulder 46 provided at the distal end of the second passage 38. In some embodiments, the shoulder 46 extends continuously peripherally around the proximal opening into the second passage 38 and in other embodiments, the shoulder 46 is discontinuous around the periphery of the proximal opening into the second passage 38.

The resilient element 28 is disposed between the first articulation surface 26 and the end portion 24. Because it is between these elements, the resilient element 28 is held in place by the same forces that serve to secure the first articulation surface 26 to the end portion 28, as discussed above. The resilient element 28 is retained against the end portion 24 by the first articulation surface 26. Resilient element 28 may also be attached to the first articulation surface 26 and/or the end portion 24 by other mechanical connections, such as clips, straps, or the like, or by adhesive, glue, epoxy, or the like, or by chemical bonding.

The first articulation surface 26 and the second articulation surface 32 are configured to cooperatively engage or abut or otherwise communicate. As shown in FIG. 1, the first articulation surface 26 is convex and the second articulation surface 32 is concave so that the convex first articulation surface 26 fits into the second articulation surface 32. As illustrated, the radius of curvature of the first articulation surface 26 is less than the radius of curvature of the second articulation surface 32. In other embodiments, the radius of curvature of the first articulation surface 26 is larger than the radius of curvature of the second articulation surfaces 32. In one embodiment, the curvature of the first articulation surface 26 is spherical. In one embodiment, the curvature of the second articulation surface 32 is spherical. For both the first and the second articulation surface 26, 32, non-spherical surfaces may be selected without departing from the spirit and scope of the invention.

Figure 2:
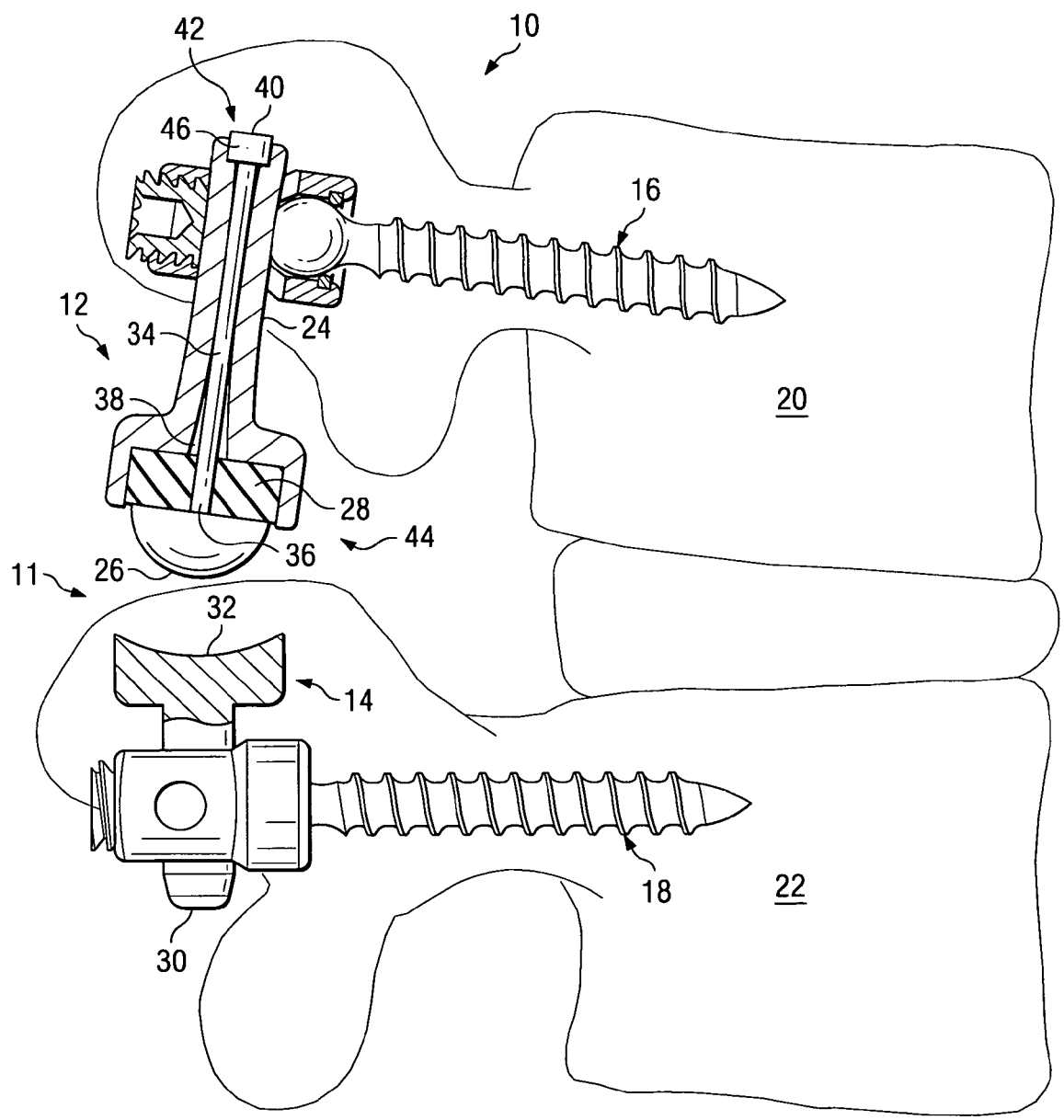
FIG. 2 is an elevational view in partial cross-section of a dynamic stabilization system and device according to one embodiment of the present invention in a flexion position.

In the neutral position illustrated in FIG. 1, the resilient element 28 is neither compressed nor extended when the system is attached across two adjacent vertebrae 20, 22, making up a spinal motion segment. This is the position, for example, when the spinal motion segment is at rest. FIG. 2 illustrates the situation in which the spinal motion segment is in flexion and the first bone anchor assembly 16 and the second bone anchor assembly 18 are moved away from each other. This would occur, for example, when the spine is being bent forward. In this situation, the first articulation surface 26 separates from the engagement with the second articulation surface 32. There is no resistance to the movement of the first articulation surface 26 and the second articulation surface 32 away from each other and the resilient element 28 is neither compressed nor extended. Note that when the articulation surfaces 26, 32 are again brought together, the curvature of the articulation surfaces 26, 32 serve to bring these articulation surfaces 26, 32 back into abutment or engagement.

Figure 3:
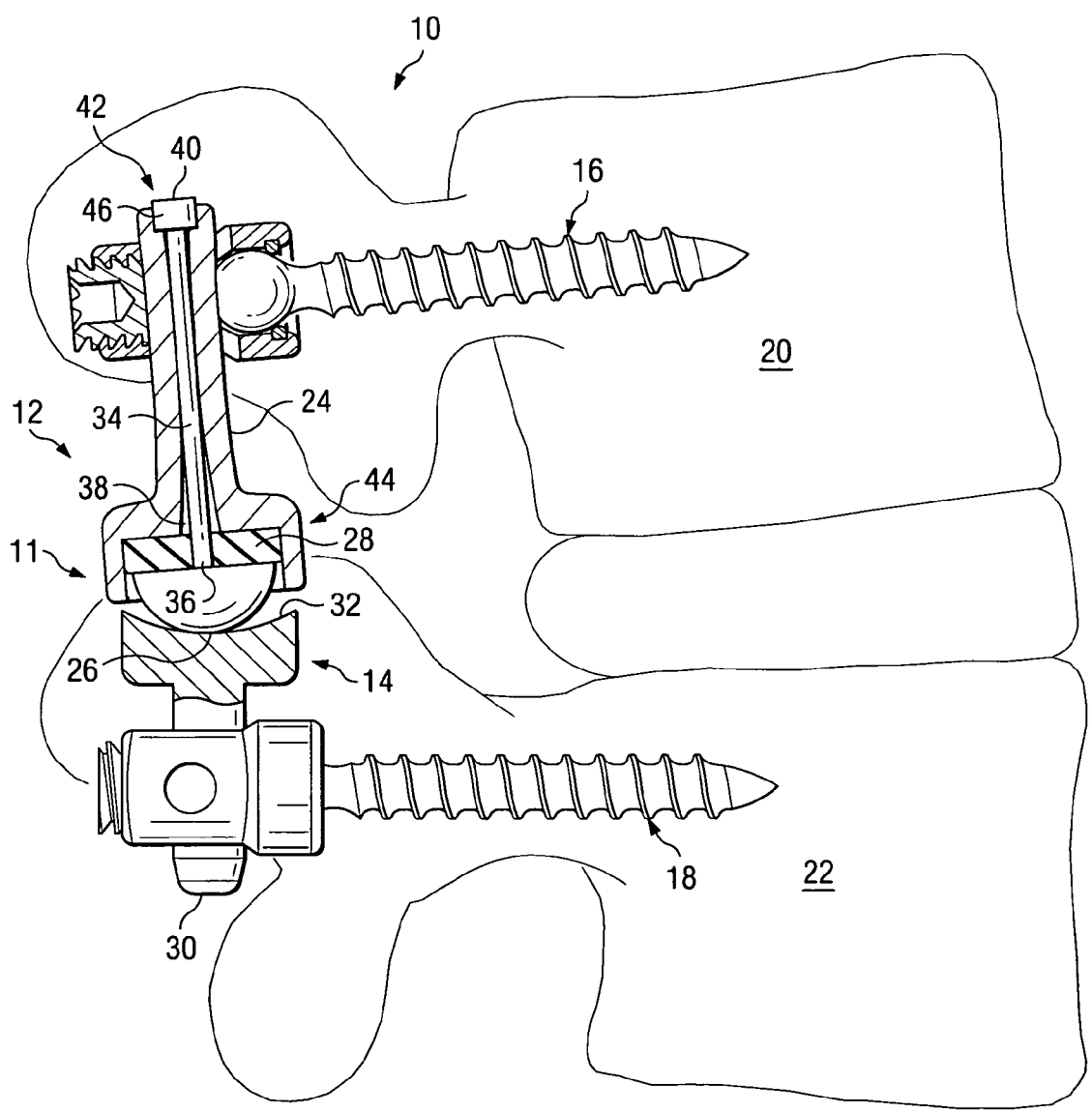
FIG. 3 is an elevational view in partial cross-section of a dynamic stabilization system and device according to one embodiment of the present invention in an extension position.

FIG. 3 illustrates the situation in which the spinal motion segment is in extension, such as when the spine is bent backward. In this situation, the first articulation surface 26 and the second articulation surface 32 engage and are pressed together. In this situation, the resilient element 28 compresses due to the force exerted by the first articulation surface 26 and the second articulation surface 32. The resilient element 28 resiliently resists the movement of the first bone anchor assembly 16 toward the second bone anchor assembly 18 and becomes compressed. This allows some controlled movement of the spine while providing stabilization and not allowing the bone anchor assemblies 16, 18, and the vertebrae 20, 22 to which they are attached, to press too close together.

When the compressive force on the resilient element 28 is lessened or removed, such as a return of the spine to a neutral or flexion position, the resilient element 28 resumes its unstressed or uncompressed shape.

In some embodiments, the spinal dynamic stabilization system 10 is implanted posteriorly, on either the left or right side of the spinal column, for example, using pedicle screws with the bone anchor systems. In some embodiments, a second system 10 is implanted on the other side of the spinal column such that the entire system 10 includes two sets of bilaterally placed elements. In these embodiments, lateral bending will result in the first articulation surface 26 and the second articulation surface 32 moving toward each other on one side and away from each other on the other side, again providing spinal stabilization.

Figure 4:
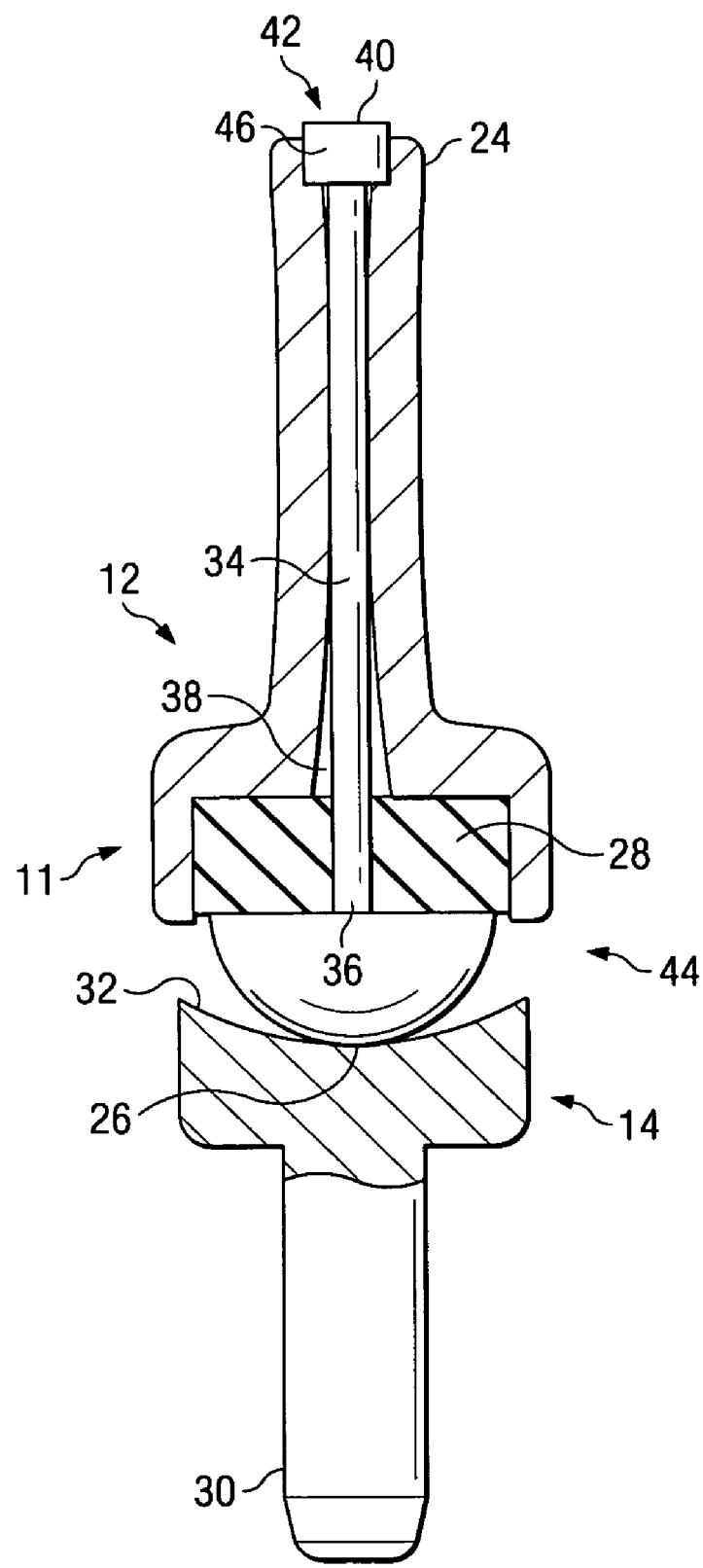
FIG. 4 is an elevational view in partial cross-section of a device according to one embodiment of the present invention.

FIG. 4 illustrates an exemplary device 11 that includes the first articulation element 12 and the second articulation element 14 described above. In this embodiment, the first articulation surface 12 and the second articulation surface 14 are attachable to one or more anchor systems to anchor the device 11 to one or more substrates. The substrates may be living or non-living.

The cross-sectional shape of the resilient element 28 may be circular, oval, or polygonal without departing from the spirit and scope of the invention. It is preferable, but not necessary, for the cross-sectional shape of the resilient element 28 at the point of contact with the end portion 24 to match the cross-sectional shape of the end portion 24 at the point of contact with the resilient element 28. The cross-sectional shape of the resilient element 28 may vary along its length.

While the invention has been described with the first bone anchor assembly 16 configured for engagement with a first human vertebra 20 and the second bone anchor assembly 18 configured for engagement with a second human vertebra 22, other embodiments contemplate elements 20, 22 to include cadaveric vertebrae, sawbones, plastic, or other vertebral replicas, or other non-living substrates.

The second articulation element 14 may be integral with the second bone anchor assembly 18 or may be a separate element attached or attachable to the second bone anchor assembly 18.

In operation, a user will install the first bone anchor assembly 16 and the second bone anchor assembly 18 in a first vertebra or substrate 20 and a second vertebra or substrate 22. The user positions the first articulation element 12 such that the end portion 24 is connectable to the first bone anchor assembly 16 and the first articulation surface 26 is separably engageable with the second articulation surface 32 attached to or integral with the second bone anchor assembly 18. The end portion 24 is connected to the first bone anchor assembly 16. As noted above, in some embodiments the vertebrae/substrates 20, 22 are living and in some embodiments, the vertebrae/substrates 20, 22 are non-living. Implantation in living substrates, such as adjacent vertebrae, is to provide dynamic stabilization of the substrates. Implantation in non-living substrates could be for training, evaluation, development, or any other reason.

In one embodiment, the dynamic stabilization system 10 is configured to be implanted into a living patient using pedicle screws implanted into adjacent vertebrae via a posterior approach.

The first articulation surface 26 and the second articulation surface 32 may be arranged so that when the vertebrae/substrates 20, 22 are in a neutral position, the end first articulation surface 26 and the second articulation surface 32 abut. Or the first articulation surface 26 and the second articulation surface 32 may be arranged so that when the substrates are in a neutral position, the first articulation surface 26 and the second articulation surface 32 are separated and do not abut. A neutral position would be, for example, when a vertebral motion segment is at rest. In another embodiment, the first articulation element 12 is constructed so the resilient element 28 has a compressive pre-load so that a distractive force is exerted on the spine after implantation.

When the first bone anchor assembly 16 and the second bone anchor assembly 18 are moved toward each other, such as during extension of a spinal motion segment to which the system 10 is attached, the first articulation surface 26 and the second articulation surface 32 abut and engage. As the first bone anchor assembly 16 and the second bone anchor assembly 18 continue to have force applied to be moved toward each other, the resilient element 28 resists such movement and deflects to provide a dampening effect on the movement. As the first bone anchor assembly 16 and the second bone anchor assembly 18 are moved away from each other, the resilient element 28 substantially returns to its original shape.

As the first bone anchor assembly 16 and the second bone anchor assembly 18 are moved away from each other, whether the first articulation surface 26 and the second articulation surface 32 are in abutment or not, the system 10 provides no resistance to this movement. Thus, if the system 10 is attached to a vertebral motion segment, there is no resistance to flexion of the spine. In some embodiments, as the first bone anchor assembly 16 and the second bone anchor assembly 18 are moved away from each other, the first articulation surface 26 is separated from and no longer abuts, or engages, the second articulation surface 32. The first articulation surface 26 is configured to be separable from and unattached to the second articulation surface 32.

Although reference is made herein to use of the dynamic stabilization system 10 with adjacent vertebrae, or a spinal motion segment, some embodiments include use of the dynamic stabilization system 10 of the present invention across non-adjacent vertebrae, or multi-level, or across more than a single spinal motion segment. The size and scale of the components, the placement of the bone anchor assemblies, etc., will be different than that for a single motion segment with adjacent vertebrae. Likewise, the size, scale, placement, etc., for use with a single motion segment with adjacent vertebrae will be different depending on what specific motion segment and adjacent vertebrae are involved. For example, the size and spacing for the L4-L5 motion segment are different that the size and spacing for the L1-L2 motion segment and mat also vary from patient to patient or substrate to substrate. These size, scale, placement, etc., differences can be determined by one of ordinary skill in the art without undue experimentation.

The form, shape, and the material of construction of the end portion 24, the resilient element 28, and the connector 34 can be selected based on criteria chosen by the user without departing from the spirit or scope of the invention. Some suitable materials are included in U.S. Ser. No. 11/028,999, identified above.

Examples of material that can be used for the end portion 24, the first articulation surface 26, and the second articulation surface 32 include cobalt-chromium alloys, titanium alloys, nickel titanium alloys, and/or stainless steel alloys, any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. Preferably, the first articulation surface 26 is made of PEEK with an integral connector 34, and the second articulation surface and the end portion 24 are made from a titanium alloy.

Resilient element 28 may be of any shape, such as cylindrical, conical, or prismatic, including rectangular, pentagonal, hexagonal, etc. prisms. The resilient element 28 is, for example, flexible, compressible, resilient, or elastic (inclusive) to permit motion of the spinal motion segment with which it is associated while providing a desired stabilization effect. The resilient element 28 can be constructed such that it has a gradual or otherwise variable stiffness. Examples of material that can be used include any suitable biocompatible elastomer or polymer biomaterial, such as surgical latex, chloroprene, MIT's "biorubber" (glycerol and sebacic acid), polyethylene, polyester, polyurethane, urethane, polypropylene, polycarbonate urethane, silicone, or hydrogel, and combinations thereof. Preferably, the resilient element 28 is a silicone or a polyurethane. The resilient element 28 can also be constructed in the form of a spring or any other shape exhibiting elastomeric properties from any suitable material. Examples of such material include cobalt-chromium alloys, titanium alloys, nickel titanium alloys, and/or stainless steel alloys.

The connector 34 may be flexible or inflexible, elastic, inelastic, or semi-elastic and of any suitable form, such as a wire, rope, cord, band, belt, suture, bar, cable, solid or hollow rod, mesh, fabric, or other suitable form and may be a metal cable, such as a titanium or titanium alloy cable. The connector 34 can be single strand, multiple strands, braided, or combinations thereof and constructed of any suitable material, preferably a biocompatible material. Examples of possible materials include but is not limited to woven or non-woven polymers, such as polyester, polyethylene, or any member of the polyaryletherketone (PAEK) family such as polyetheretherketone (PEEK), carbon-reinforced PEEK, or polyetherketoneketone (PEKK), polysulfone; polyetherimide, polyimide, ultra-high molecular weight polyethylene (UHMWPE), and/or cross-linked UHMWPE; superelastic metals, such as nitinol; shape memory alloy, such as nickel titanium; resorbable synthetic materials, such as suture material, metals, such as stainless steel and titanium; synthetic materials, allograft material; and bioelastomer material. Preferably, the connector 34 is integral with the PEEK first articulation surface 26.

Any combination of features from the embodiments described above is also within the spirit and scope of the invention and such combinations and configurations will be apparent to one of ordinary skill in the art without undue experimentation to accomplish the specific results and parameters of particular circumstances present or contemplated.

While the present invention has been illustrated by the above description of embodiments, and while the embodiments have been described in some detail, it is not the intention of the applicant to restrict or in any way limit the scope of the invention to such detail. For example, the relative positioning of the first articulation element and the second articulation element as described above can be switched. Additional advantages and modifications will readily appear to those skilled in the art. Therefore, the invention in its broader aspects is not limited to the specific details, representative apparatus and methods, and illustrative examples shown and descried. Accordingly, departures may be made from such details without departing from the spirit or scope of the applicant's general or inventive concept.

We claim:

1. A bone anchor-based spinal dynamic stabilization system, comprising:
   a. a first bone anchor assembly engageable with a first vertebra;
   b. a second bone anchor assembly engageable with a second vertebra;
   c. a first articulation element attachable to the first bone anchor assembly, the first articulation element comprising:
      i. an end portion for attachment to the first bone anchor assembly;
      ii. a first articulation surface; and
      iii. a resilient element disposed between the end portion and the first articulation surface;
      iv. a connector engaging the first articulation surface and extending from the first articulation surface disposed through a first passage in the resilient element and through a second passage in the end portion to terminate in the end portion, the connector adapted to connect the first articulation surface to the end portion; and
   d. a second articulation element attachable to the second bone anchor assembly and having a second articulation surface configured to engage the first articulation surface; wherein the first articulation surface is configured to be separably engageable with the second articulation surface and is positioned between the end portion of the first articulation element and the second articulation surface; and wherein the resilient element is configured to resiliently resist movement of the first bone anchor assembly and the second bone anchor assembly towards each other when the first articulation surface and the second articulation surface are engaged with each other and the first articulation element and the second articulation element are attached to the first bone anchor assembly and the second bone anchor assembly, respectively;

wherein the system is configured to provide no resistance to movement of the first bone anchor assembly and the second bone anchor assembly away from each other.

2. The spinal dynamic stabilization system of claim 1, wherein the first articulation surface is secured to the end portion.

3. The spinal dynamic stabilization system of claim 2, further comprising a connector that secures the first articulation surface to the end portion, the connector engaged with the end portion and the first articulation surface.

4. The spinal dynamic stabilization system of claim 3, wherein the resilient element comprises a passage at least partially therethrough, the end portion comprises a passage at least partially therethrough, and the connector is disposed within the passage of the resilient element and the passage of the end portion to secure the first articulation surface to the end portion.

5. The spinal dynamic stabilization system of claim 4, wherein the connector is crimped within the passage of the end portion.

6. The spinal dynamic stabilization system of claim 4, wherein the connector comprises a head disposed at a proximal end of the end portion away from the first articulation surface and is configured to retain the first articulation surface against the end portion.

7. The spinal dynamic stabilization system of claim 3, wherein the connector is integral with the first articulation surface.

8. The spinal dynamic stabilization system of claim 3, wherein the connector is a tether.

9. The spinal dynamic stabilization system of claim 1, wherein the resilient element is disposed between the first articulation surface and the end portion and is retained against the end portion by the first articulation surface.

10. The spinal dynamic stabilization system of claim 1, wherein the first and second bone anchor assemblies comprise pedicle screws.

11. The spinal dynamic stabilization system of claim 1, wherein one of the first and second articulation surfaces includes a convex shape and the other of the first and second articulation surfaces includes a concave shape to form a ball-and-socket joint.

12. A device for use within a spinal dynamic stabilization system, the device comprising:
  a. a first articulation element comprising:
    i. an end portion;
    ii. a first articulation surface; and
    iii. a resilient element disposed between the end portion and the first articulation surface; and
    iv. a connector engaging the first articulation surface and extending from the first articulation surface disposed through the first passage in the resilient element and through a second passage in the end portion to terminate in the end portion, the connector adapted to secure the first articulation surface to the end portion;
  b. a second articulation element having a second articulation surface configured to engage the first articulation surface;
  wherein the first articulation surface is configured to be separably engageable with the second articulation surface and is positioned between the end portion of the first articulation element and the second articulation surface; and wherein the resilient element is configured to resiliently resist compression of the first articulation surface against the second articulation surface when they are engaged with each other.
  wherein the end of the connector faces towards the second articulation element and the connector is configured for the end portion to move away from the second articulation surface when the first and second articulation elements move away from each other.

13. The device of claim 12, wherein the resilient element is engaged to the end portion.

14. The device of claim 13, wherein the resilient element comprises a passage at least partially therethrough, the end portion comprises a passage at least partially therethrough, and the connector is disposed within the passage of the resilient element and the passage of the end portion to attach the resilient element to the end portion.

15. The device of claim 14, wherein the connector is crimped within the passage of the end portion.

16. The device of claim 14, wherein the connector comprises a head disposed at a proximal end of the end portion away from the first articulation surface and is configured to retain the first articulation surface against the end portion.

17. The device of claim 13, wherein the first articulation element is attachable to a first anchor system to anchor the first articulation element to a first substrate and the second articulation element is attachable to a second anchor system to anchor the second articulation element to a second substrate.

18. The device of claim 13, wherein the second articulation element is integral with a second anchor system configured to anchor the second articulation element to a substrate.

19. A method of installing a dynamic stabilization system, comprising
  a. providing the spinal dynamic stabilization system of claim 1;
  b. installing the first bone anchor assembly in a first substrate;
  c. installing the second bone anchor assembly in a second substrate;
  d. positioning the first articulation element with the second articulation element, the second articulation element being attached to the second, bone anchor assembly; and
  e. connecting the end portion of the first articulation element to the first bone anchor assembly;
  f. compressing the resilient element during movement of the first bone anchor assembly towards the second bone anchor assembly; and
  g. moving the connector away from the second articulation element during movement of the first bone anchor assembly away from the second bone anchor assembly.

20. The method of claim 19, wherein the first substrate and the second substrate are non-living.

* * * * *